(12) United States Patent
Stroppolo et al.

(10) Patent No.: US 8,747,894 B2
(45) Date of Patent: Jun. 10, 2014

(54) EFFERVESCENT COMPOSITIONS CONTAINING N-ACETYLCYSTEINE

(75) Inventors: Federico Stroppolo, Aldesago (CH); Gabriele Granata, Leggiuno (IT); Shahbaz Ardalan, Massagno (CH)

(73) Assignee: Alpex Pharma S.A., Meezovico (CH)

( * ) Notice: Subject to any disclaimer, the term of this patent is extended or adjusted under 35 U.S.C. 154(b) by 0 days.

(21) Appl. No.: 13/466,721

(22) Filed: May 8, 2012

(65) Prior Publication Data

US 2013/0302259 A1    Nov. 14, 2013

(51) Int. Cl.
*A61K 9/46* (2006.01)
*A61P 39/02* (2006.01)
*A61K 31/198* (2006.01)

(52) U.S. Cl.
USPC .......................................................... 424/466

(58) Field of Classification Search
USPC .......................................................... 424/466
See application file for complete search history.

(56) References Cited

U.S. PATENT DOCUMENTS

| 6,566,401 | B2 | 5/2003 | Herzenberg et al. |
| 6,719,969 | B1 | 4/2004 | Hogaboam et al. |
| 7,723,389 | B2 | 5/2010 | Herzenberg et al. |
| 2007/0049640 | A1 | 3/2007 | Pavliv |

FOREIGN PATENT DOCUMENTS

| WO | WO 2010/090612 | * | 8/2010 | ............. A61K 47/04 |
| WO | WO 2011/128230 | * | 10/2011 | ............... A61K 9/00 |

* cited by examiner

*Primary Examiner* — Rachael E Bredefeld
(74) *Attorney, Agent, or Firm* — Lucas & Mercanti, LLP

(57) ABSTRACT

Effervescent pharmaceutical compositions containing a high amount of N-acetylcysteine and a method of treating acetaminophen poisoning with effervescent pharmaceutical compositions containing a high amount of N-acetylcysteine are described.

17 Claims, No Drawings

EFFERVESCENT COMPOSITIONS CONTAINING N-ACETYLCYSTEINE

FIELD OF THE INVENTION

The present invention relates to effervescent pharmaceutical compositions containing N-acetylcysteine, more particularly to effervescent compositions containing a high amount of N-acetylcysteine useful for the oral treatment of acetaminophen poisoning.

BACKGROUND OF THE INVENTION

N-acetylcysteine (NAC) is a well-known drug approved worldwide for several indications mainly as mucolytic agent but it is also one of the few available treatments for acetaminophen poisoning.

Acetaminophen (paracetamol) is a commonly used analgesic and antipyretic drug. Accidental or suicidal acetaminophen overdose can cause severe liver damage which result in several deaths each year in the U.S.A.

NAC is effective by intravenous or oral route for the treatment of acetaminophen poisoning if administered within 8-10 hours of acetaminophen overdose. The dose of NAC to be administered is very high according to the Prescott therapy protocol, as reported in the following table 1:

TABLE 1

NAC doses according to the Prescott therapy protocol

| Body weight (kg) | NAC loading dose (g) | NAC maintenance dose (g) |
| --- | --- | --- |
| 100-109 | 15 | 7.5 |
| 90-99 | 14 | 7 |
| 80-89 | 13 | 6.5 |
| 70-79 | 11 | 5.5 |
| 60-69 | 10 | 5 |
| 50-59 | 8 | 4 |
| 40-49 | 7 | 3.5 |
| 30-39 | 6 | 3 |
| 20-29 | 4 | 2 |

The only available NAC dosage form for the treatment of acetaminophen poisoning is Acetadote®, 30 ml vials containing 200 mg/ml NAC for intravenous administration.

The oral treatment of acetaminophen poisoning with NAC is equally or even more effective than intravenous treatment when administered within 8-10 hours of acetaminophen overdose (Michele Zell Kanter, American Journal of Health—System Pharmacy, Oct. 1, 2006 vol. 63 no. 19, 1821-1827), the contents of which are incorporated herein by reference and would be more practical and safer. However, the very high dosage limits the possibility to use commercially available NAC formulations for oral administration which usually have a maximum NAC content of 600 mg.

Therefore, it would be desirable to have an oral formulation containing a high amount of NAC to be used for the treatment of acetaminophen poisoning.

SUMMARY OF THE INVENTION

We have now found an effervescent composition containing a high amount of NAC which is very easy to administer as an aqueous solution and is particularly useful for the oral treatment of acetaminophen poisoning.

In a first aspect, the present invention relates to an effervescent composition containing at least 50% w/w of NAC, at least 20% w/w of a carbonate or bicarbonate salt and a mixture of pharmaceutically acceptable excipients comprising a sweetener, a flavor, and a diluent.

In a further aspect, the present invention relates to a method of treating acetaminophen poisoning. The method includes administering an effective amount of an effervescent composition containing at least 50% w/w of NAC, at least 20% w/w of a carbonate or bicarbonate salt and a mixture of pharmaceutically acceptable excipients comprising a sweetener, a flavor, and a diluent to a patient in need of such treatment.

DETAILED DESCRIPTION OF EMBODIMENTS OF THE INVENTION

The present invention relates to an effervescent composition containing a high amount of NAC which is particularly useful for the oral treatment of acetaminophen poisoning.

The effervescent composition and object of the present invention contains at least 50% w/w of NAC, at least 20% w/w of a carbonate or bicarbonate salt and a mixture of pharmaceutically acceptable excipients comprising a sweetener, a flavor, and a diluent.

As used herein, a value % w/w means the weight percent of a component of the composition with respect to the total weight of said composition.

In a preferred embodiment, the amount of NAC in the effervescent composition ranges from 50% to 80% w/w, more preferably, it is from 50% to 60% w/w.

In a particularly preferred embodiment of the present invention, the amount of NAC is about 54-55% w/w.

Suitable carbonate or bicarbonate salts are pharmaceutically acceptable carbonate or bicarbonate salts commonly used as $CO_2$ source in effervescent compositions.

Specific examples include sodium bicarbonate, sodium carbonate, potassium bicarbonate, potassium carbonate, sodium sesquicarbonate ($NaHCO_3+Na_2CO_3+2H_2O$), sodium glycine carbonate and the like.

Sodium bicarbonate is particularly preferred.

The amount of carbonate or bicarbonate salt in the effervescent compositions according to the present invention is at least 20% w/w, preferably from 20% to 45% w/w, and more preferably from 30% to 35% w/w.

The Applicant has found that the formulation of the present invention develops effervescence in water without the need of an additional organic or inorganic acid, making it particularly advantageous in comparison with known effervescent NAC compositions which require the presence of an effervescent couple.

In addition to the active ingredient and the carbonate or bicarbonate salt, the effervescent composition of the present invention usually contains a mixture of excipients comprising a sweetener, a flavor, and a diluent.

The total amount of the additional excipients is usually from 3.5% to 15% w/w.

Suitable sweeteners include sugars, such as mono- or di-saccharides, for example glucose, saccharose, maltose, galactose, and artificial sweeteners, such as sodium saccharin, acesulfame potassium, cyclamates, sucralose. Artificial sweeteners are preferred, and among them sucralose is particularly preferred.

The amount of sweetener ranges from 0.2% to 10% w/w, and preferably is from 0.5% to 1% w/w.

The amount of flavor ranges from 1% to 3% w/w, and preferably is about 2% w/w.

Any pharmaceutically acceptable flavors can be used such as fruit flavor, peppermint flavor, etc. Fruit flavors are preferred, and lemon and orange flavors are particularly preferred.

Suitable diluents include polyols, such as for example mannitol, sorbitol, xylitol, as well as cellulose, starch and maltodextrin.

Maltodextrin is particularly preferred.

The amount of diluent usually ranges from 2% to 20% w/w.

The effervescent composition according to the present invention can optionally contain further pharmaceutically acceptable excipients such as chelating agents, for example EDTA, lubricants, for example sodium benzoate and magnesium stearate, colorants, etc.

When a lubricant is present in the formulation according to the present invention, the amount of lubricant usually ranges from 0.1% to 5% w/w.

Sodium benzoate is preferably used.

The effervescent NAC compositions of the invention are prepared by conventional granulation techniques, preferably by wet granulation for example in a fluid bed granulator.

The effervescent granulate can be used as such as finished dosage form, for example filled in sachets or can be compressed into tablets.

In a preferred embodiment, the pharmaceutical NAC composition according to the invention is in the form of effervescent tablets.

The dose of NAC contained in the finished dosage unit can range from 0.5 g to 2.5 g without changing the physical properties of the solid composition.

In particular, the effervescent formulations according to the present invention are readily soluble in a small amount of water, have a good taste and are of limited dimensions to be easily stored and transported.

The unit dose of NAC can be for example 0.5 g, 1.0 g, 1.5 g, 2.0 g and 2.5 g. Unit doses of 0.5 g and 2.5 g are particularly preferred because they can be easy combined to reach any therapeutic dose required by the Prescott therapy protocol as reported in the following table 2.

TABLE 2

| Body weight (Kg) | NAC (g) | Number of tablets of the invention (2.5 g NAC/tablet) | Number of tablets of the invention (0.5 g NAC/tablet) | Volume of reconstituted solution to be administered to patients |
|---|---|---|---|---|
| Loading dose | | | | |
| 100-109 | 15 | 6 | 0 | About 200 mL (a glass of water) |
| 90-99 | 14 | 5 | 3 | |
| 80-89 | 13 | 5 | 1 | |
| 70-79 | 11 | 4 | 2 | |
| 60-69 | 10 | 4 | 0 | |
| 50-59 | 8 | 3 | 1 | |
| 40-49 | 7 | 2 | 4 | |
| 30-39 | 6 | 2 | 2 | |
| 20-29 | 4 | 1 | 3 | |
| Maintenance dose | | | | |
| 100-109 | 7.5 | 3 | 0 | About 200 mL (a glass of water) |
| 90-99 | 7 | 2 | 4 | |
| 80-89 | 6.5 | 2 | 3 | |
| 70-79 | 5.5 | 2 | 1 | |
| 60-69 | 5 | 2 | 0 | |
| 50-59 | 4 | 1 | 3 | |
| 40-49 | 3.5 | 1 | 2 | |
| 30-39 | 3 | 1 | 1 | |
| 20-29 | 2 | 0 | 4 | |

The above table clearly shows some of the most significant advantages of the effervescent composition of the present invention in the treatment of acetaminophen poisoning.

The high content of NAC of the compositions together with their very high solubility results in the possibility to easy adjust the administered dose according to the therapy protocol by calculating the number of tablets (as multiple of the 2.5 g dose and/or as multiple of the 0.5 g dose) and to dissolve it into a glass of water.

The resultant solution contains the therapeutic dose of NAC, has a good taste, is very easy to administer to the patient.

The possibility to administer the effervescent compositions of the invention in a glass of water is a remarkable advantage over the commercially available NAC formulations used for the treatment of acetaminophen poisoning.

The required therapeutic dose is very easy to calculate in terms of number of tablets or sachets to dissolve.

The glass of water containing a therapeutic dose of NAC has a good taste (good patient compliance also in case of children) and does not require trained nurses to be administered, as in the case of NAC vials.

The following examples better illustrate the present invention without limiting it.

EXAMPLE 1

NAC (543 g), sodium bicarbonate (348 g), maltodextrin (79.8 g), sucralose (7 g), and EDTA sodium (0.2 g) were granulated together with water in a fluid bed granulator.

The granulate was then dried until a residual moisture content of not more than 0.5%, unloaded from the fluid bed and blended with sodium benzoate (3 g) and orange flavor (19 g).

The resultant mixture was compressed into flat round tablets, 25 mm diameter, weighing 4.6 g and containing 2.5 g NAC or into flat round tablets, 14 mm diameter, weighing 0.92 g and containing 0.5 g NAC.

EXAMPLE 2

NAC (543 g), sodium bicarbonate (348.2 g), maltodextrin (79.8 g), and sucralose (7 g) were granulated together with water in a fluid bed granulator.

The granulate was then dried until a residual moisture content of not more than 0.5%, unloaded from the fluid bed and blended with sodium benzoate (3 g) and orange flavor (19 g).

The resultant mixture was compressed into flat round tablets, 25 mm diameter, weighing 4.6 g and containing 2.5 g NAC or into flat round tablets, 14 mm diameter, weighing 0.92 g and containing 0.5 g NAC.

EXAMPLE 3

NAC (543 g), sodium bicarbonate (351 g), maltodextrin (79.8 g), sucralose (7 g), and EDTA sodium (0.2 g) were granulated together with water in a fluid bed granulator.

The granulate was then dried until a residual moisture content of not more than 0.5%, unloaded from the fluid bed and blended with orange flavor (19 g).

The resultant mixture was compressed into flat round tablets, 25 mm diameter, weighing 4.6 g and containing 2.5 g NAC or into flat round tablets, 14 mm diameter, weighing 0.92 g and containing 0.5 g NAC.

EXAMPLE 4

NAC (543 g), sodium bicarbonate (351.2 g), maltodextrin (79.8 g), and sucralose (7 g), were granulated together with water in a fluid bed granulator.

The granulate was then dried until a residual moisture content of not more than 0.5%, unloaded from the fluid bed and blended with orange flavor (19 g).

The resultant mixture was compressed into flat round tablets, 25 mm diameter, weighing 4.6 g and containing 2.5 g NAC or into flat round tablets, 14 mm diameter, weighing 0.92 g and containing 0.5 g NAC.

EXAMPLE 5

NAC (543 g), sodium bicarbonate (351 g), maltodextrin (79.8 g), sucralose (7 g), and EDTA sodium (0.2 g) were granulated together with water in a fluid bed granulator.

The granulate was then dried until a residual moisture content of not more than 0.5%, unloaded from the fluid bed and blended with orange flavor (19 g).

The resultant mixture was filled into paper/aluminum sachets, 40×60 mm, weighing 4.6 g and containing 2.5 g NAC or weighing 0.92 g and containing 0.5 g NAC.

EXAMPLE 6

NAC (543 g), sodium bicarbonate (351.2 g), maltodextrin (79.8 g), and sucralose (7 g) were granulated together with water in a fluid bed granulator.

The granulate was then dried until a residual moisture content of not more than 0.5%, unloaded from the fluid bed and blended with orange flavor (19 g).

The resultant mixture was filled into paper/aluminum sachets, 40×60 mm, weighing 4.6 g and containing 2.5 g NAC or weighing 0.92 g and containing 0.5 g NAC.

What is claimed is:

1. An oral effervescent composition comprising at least 50% w/w of N-acetylcysteine, at least 20% w/w of a carbonate or bicarbonate salt, without an additional organic or inorganic acid, and a mixture of pharmaceutically acceptable excipients comprising a sweetener, a flavor, and a diluent, wherein the carbonate or bicarbonate salt is selected from the group consisting of sodium bicarbonate, sodium carbonate, potassium bicarbonate, potassium carbonate, sodium sesquicarbonate, and sodium glycine carbonate.

2. The effervescent composition according to claim 1 wherein the amount of N-acetylcysteine is from 50% to 80% w/w.

3. The effervescent composition according to claim 2 wherein the amount of N-acetylcysteine is from 50% to 60% w/w.

4. The effervescent composition according to claim 3 wherein the amount of N-acetylcysteine is from 54% to 55% w/w.

5. The effervescent composition according to claim 1 wherein the bicarbonate salt is sodium bicarbonate.

6. The effervescent composition according to claim 1 wherein the amount of carbonate or bicarbonate salt is from 20% to 45% w/w.

7. The effervescent composition according to claim 6 wherein the amount of carbonate or bicarbonate salt is from 30% to 35% w/w.

8. The effervescent composition according to claim 1 wherein the sweetener is selected from the group consisting of sugars and artificial sweeteners.

9. The effervescent composition according to claim 8 wherein the artificial sweetener is selected from the group consisting of sodium saccharin, acesulfame potassium, cyclamates, and sucralose.

10. The effervescent composition according to claim 9 wherein the artificial sweetener is sucralose.

11. The effervescent composition according to claim 1 wherein the diluent is selected from the group consisting off polyols, cellulose, starch and maltodextrin.

12. The effervescent composition according to claim 11 wherein the diluent is maltodextrin.

13. The effervescent composition according to claim 1 further comprising a lubricant.

14. The effervescent composition according to claim 13 wherein the lubricant is sodium benzoate.

15. A method of treating acetaminophen poisoning, comprising administering an effective amount of effervescent composition containing at least 50% w/w of N-acetylcysteine, at least 20% w/w of a carbonate or bicarbonate salt, without an additional organic or inorganic acid, and a mixture of pharmaceutically acceptable excipients comprising a sweetener, a flavor, and a diluent to a patient in need thereof, wherein the carbonate or bicarbonate salt is selected from the group consisting of sodium bicarbonate, sodium carbonate, potassium bicarbonate, potassium carbonate, sodium sesquicarbonate, and sodium glycine carbonate.

16. The method according to claim 15 wherein the effervescent composition contains a unit-dose of N-acetylcysteine of 0.5 g, 1.0 g, 1.5 g, 2.0 g, or 2.5 g.

17. The method according to claim 16 wherein the unit-dose is 0.5 or 2.5 g.

* * * * *